United States Patent

Sekiguchi et al.

[11] Patent Number: 5,201,214
[45] Date of Patent: Apr. 13, 1993

[54] ROTARY VISCOSIMETER HAVING PIVOT PROTECTION APPARATUS

[75] Inventors: Koji Sekiguchi, Komae; Yoshihiro Kato, Chiba, both of Japan

[73] Assignee: Toki Sangyo Co., Ltd., Tokyo, Japan

[21] Appl. No.: 758,854

[22] Filed: Sep. 12, 1991

[51] Int. Cl.⁵ .......................................... G01N 11/14
[52] U.S. Cl. .................................. 73/54.35; 73/54.33
[58] Field of Search .................. 73/54.33, 54.32, 54.34, 73/54.35, 54.28

[56] References Cited

U.S. PATENT DOCUMENTS

| 3,169,392 | 2/1965 | Brookfield | 73/54.35 |
| 3,886,789 | 6/1975 | Brookfield | 73/54.35 |

FOREIGN PATENT DOCUMENTS

| 26195 | 8/1970 | Japan | 73/54.32 |
| 52-10381 | 1/1977 | Japan | |
| 972328 | 11/1982 | U.S.S.R. | 73/54.35 |
| 2204701 | 11/1988 | United Kingdom | 73/54.28 |

Primary Examiner—Hezron E. Williams
Assistant Examiner—Joseph W. Roskos
Attorney, Agent, or Firm—Lowe, Price, LeBlanc & Becker

[57] ABSTRACT

A rotary viscosimeter includes a rotor driven to rotate in a liquid, the viscosity of which is to be measured. A first drive shaft or rotor shaft supports the rotor and transmits a rotary driving force to the rotor. A rotary driving apparatus has a motor for driving the rotor with an output shaft for supplying the driving force. A second drive shaft transmits the drive force from the motor to the rotor shaft. A first link elastically links the output shaft of the motor with the second drive shaft to transmit the driving force therebetween. A support includes a pivot and a bearing for rotatably supporting the motor shaft and second link which by-passes the support for linking the rotor shaft with the second shaft. A detector senses the angular displacement between the output shaft and the rotor shaft. A pivot protector has a locking mechanism for locking the rotor shaft from rotating and for disengaging the lock. A pivot separating mechanism separates and engages the pivot and the bearing of the support. A controller controls the motor and pivot protector.

10 Claims, 9 Drawing Sheets

0: VISCOSIMETER IS STOPPED
1: ROTOR SHAFT IS RELEASED
2: VISIOSIMETER IS MEASURING
3: ROTOR SHAFT IS CLAMPED

ROTARY VISCOSIMETER HAVING PIVOT PROTECTION APPARATUS

BACKGROUND OF THE INVENTION

1. Field of the Invention

The present invention relates to a rotary viscosimeter in which a rotor shaft and a rotor are borne by a pivot and in particular to a rotary viscosimeter having a pivot protection apparatus for protecting the pivot by separating the pivot from the bearing when no viscosity measurement is being taken.

2. Description of the Related Art

Figure 5:
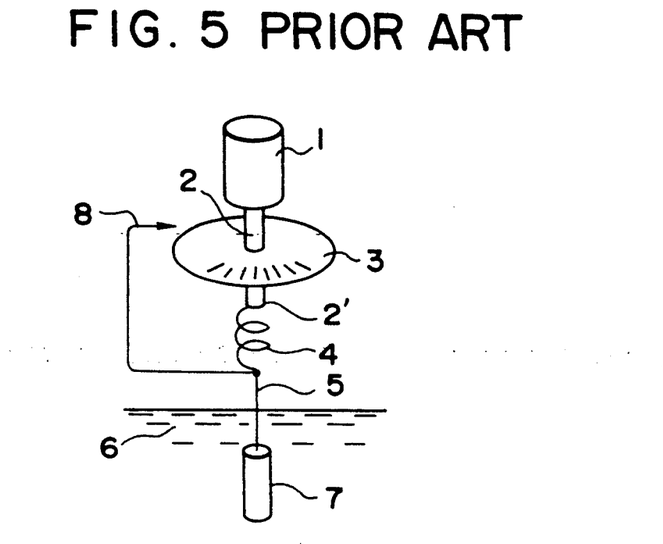
FIG. 5 is a schematic view illustrating the operation principle of the measurement of the rotary viscosimeter.

There have been developed constant sliding speed type viscosimeters as one kind of rotary viscosimeter. The principle of operation of such a type of viscosimeter for measurement will be described with reference to FIG. 5. As shown in FIG. 5, the rotary viscosimeter of this type comprises a rotary driving shaft 2 of a driving motor (for example, an electric synchronous motor) on which a graduated dial scale plate 3 is mounted, a rotor shaft 5 which is connected with the lower and 2' of the driving shaft 2 via a spring 4 and a rotor 7 secured to the lower and of the rotor shaft 5, which is immersed in a sample liquid 6, the viscosity of which is to be measured. On the other hand, a pointer needle 8 which extends radially above the graduated plate 3 is secured to the rotor shaft 5 so that the angular displacement between the driving shaft 2 and the rotor shaft 5 can be read from the position of the needle 8 on the graduated plate 3.

In the thus formed structure, the viscosity of the sample liquid 6 can be determined from the angular displacement between the rotor shaft 5 and the driving shaft when the torque generated in the rotor 7 due to the viscosity of the sample liquid 6 is balanced with the elastic force of the spring 4. That is, if the spring constant of the spring 4, the size of the rotor 7 and the rotational number are determined, the indication of the pointer needle 8 is proportional to the viscosity of the sample liquid 6. Accordingly, the viscosity of the viscous sample liquid can be determined from the indication of the pointer needle 8.

Figures 6, 7:
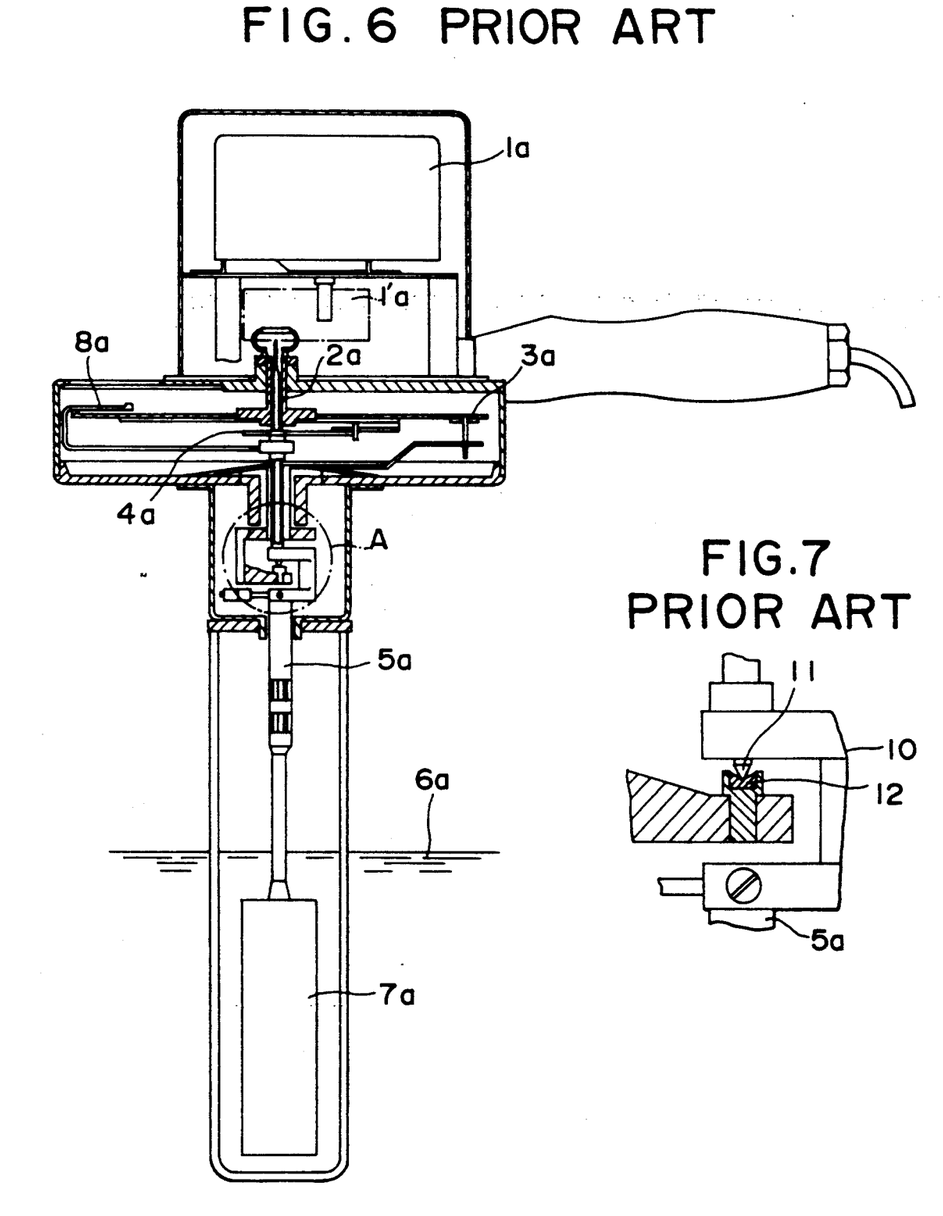
FIG. 6 is a sectional view showing the structure of a prior art rotary viscosimeter.
FIG. 7 is an enlarged view of FIG. 6.

In the foregoing description of the principle of measurement, the rotor shaft 5, the rotor 7 and the point needle 8 are linked with the lower end 2' of the driving shaft via a spring 4. The section of an actual rotary viscosimeter relying upon which the operation principle relies is shown in FIGS. 6 and 7. FIG. 7 is an enlarged view showing a part A (a pivot and its bearing) of FIG. 6.

The angular displacement of the driving shaft 2 with respect to the rotor shaft 2 can be read as the indication of the needles 8 and 8a on the graduated dial scale plates 3 and 3a as shown in FIGS. 5 and 6, respectively.

The rotor shaft 5a is borne by the pivot 11 and the bearing 12 (actually a gemstone bearing) and is linked with a pointing needle 7 extending upward via the $\pi$-shaped linking member 10. The other components such as a driving motor, a graduated dial scale plate 6, a spiral spring 4a, a sample liquid 6a, a rotor 7a and a pointer needle 8a correspond to those represented by the like reference numerals not suffixed with a in FIG. 5. A reference numeral 1' a represents the transmission of a driving motor 1a.

Since the viscosimeter is thus structured, the total weight of the rotor 7a, the rotor shaft 5a, the $\pi$-shaped link member 10, the pointer needle shaft and the pointer needle 8a secured to the rotor shaft 5a is imposed upon the contract between the pivot 11 and the bearing 12 as a thrust load. Therefore, a frictional torque is generated on rotation of the rotor shaft 5a. Since the viscosity resisting torque acting upon the rotor 9a may be very low for a specific sample liquid to be measured, pivot friction torque may give an adverse influence upon the measurement of a liquid having a low viscosity, resulting in a lowered measurement accuracy. Accordingly, efforts for reducing the frictional torque have been made by minimizing the radium of the sphere at the tip end of the pivot 11 which is in contact with the bearing 12. Since the load such as the rotor, etc. is supported at one point in such a type of viscosimeter, load conditions at the pivot are very severe in comparison with the other industrial instruments using an ordinary pivot.

The rotor 7a is removed from the rotor shaft 5a or the rotor 7a is replaced with another rotor for washing the rotor 7a after the measurement of the viscosity is completed in such type of viscosimeter. There have been problems that the pivot 11 is deformed by the application of an excessive force to the pivot 11 and damage to the bearing 12 frequently occurs in such a removing or replacing operation. There has also been a problem in that the parts are deteriorated due to vibrations and shocks on transportation of the viscosimeter.

There is also the possibility that the pivot 11 and the bearing 12 are damaged by the application of an external force when removing or mounting the rotor during exchange on normal treatment. Accordingly, operating conditions of the viscosimeter are very severe in comparison with those of the pivot of general industrial instruments. Users of the viscosimeter have to pay careful attention to the operation of the viscosimeter.

A rotary viscosimeter including a protection mechanism for protecting the pivot 11 when the rotor is removed or mounted for exchange or when the viscosimeter is transported has been devised by the present inventors and filed and patented in Japan. (Japanese Utility Model Registration Publication Sho 52-10391).

Figure 8:
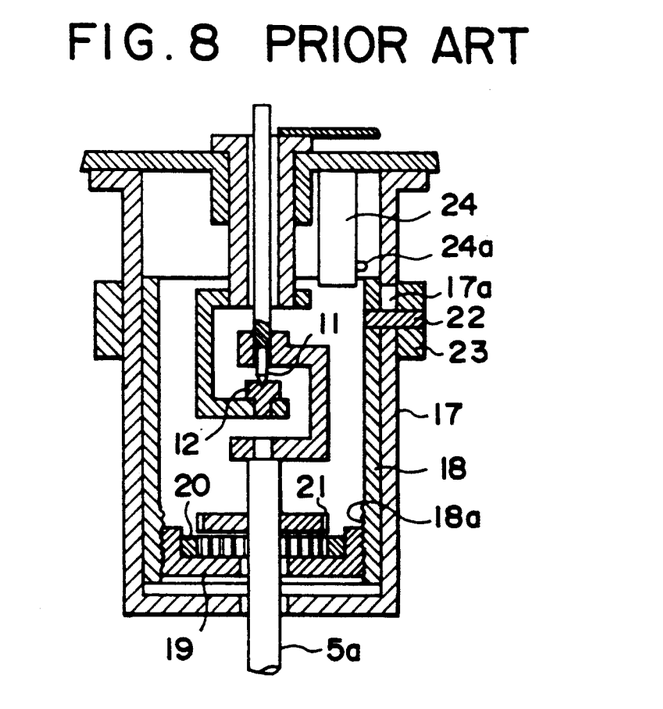
FIG. 8 is a sectional view showing a prior art pivot protection apparatus.

The pivot protection mechanism of this device is formed as shown in FIG. 8. A cylindrical sleeve 18 which is guided and is axially slidable along the inner wall of the lower casing 17 is provided in the lower casing 17 which houses a pivot 11 and its bearing 12. The sleeve 18 is formed with a thread 18a on the inner wall at the lower portion thereof. A circular disc 19 which is threaded with the internal thread 18a is provided. The disc 19 has in the center thereof a through-hole through which a rotor shaft 5a freely passes. For example, internal gear 20 serving as a lower engaging member is secured to the upper surface of the disc 19. As an upper engaging member which is engaged with the lower engaging member, an external gear 21 having the same pitch as that of the internal gear 30 is provided. The external gear 21 is secured to the rotor shaft 5a. The positions and depths of the gears 20 and 21 are determined so that the gears 20 and 21 are brought into engagement when the sleeve 18 is moved slightly upward from the lowermost position as will be described hereafter.

On the other hand, an opening 17a is provided on the side wall of the lower casing 17. A pin 22 is inserted into the opening 17a. The pin 22 has one end mounted on the sleeve 18 and the other end mounted on a ring-like grip 22 which is vertically slidable along the outer periphery of the lower casing 17. The opening 17a is formed in such a manner that when the pin 22 contacts with the lower end of the opening 17a, an engagement between the internal and external gears 20 and 21 is completely released and when the pin 22 contacts with the upper end of the opening 17a, both gears 20 and 21 are completely engaged with each other and are pushed upward by the disc 19 so that the pivot 11 is completely separated from the bearing 12.

A limit switch 24 comprises a micro-switch and has a pin 24a which is formed as a part of an actuator for the switching operation. The pin 24a is normally projected outwards and is depressed by the upper end of the sleeve 18 when the sleeve 18 is moved upward to a position where the internal and external gears 20 and 21 are brought into engagement. Depression of the pin 24a causes the limit switch 24 to be operated for turning off the power source for a motor 1a for driving the viscosimeter.

When the rotary viscosimeter is not used for measurement, the pivot 11 is separated from the bearing 12 and the rotor shaft 5a is prevented from rotating by positioning the sleeve 18 in an upper position. Accordingly, no damage is caused to the pivot 11 and the bearing 12 even on transportation of the viscosimeter or removing or mounting of the rotor 7a.

Users of the rotary viscosimeter having the above mentioned prior art pivot protection mechanism should conduct operations such as upward sliding of the ring-like grip 23 every time the rotor 7a is exchange after completion of the measurement. Particularly, upward sliding of the ring-like grip 23 for exchanging the rotor 7a is important. There is the possibility that the pivot 11 and/or its bearing 12 may be damaged if there is a failure to carry out the manual sliding operation and the exchange of the rotors is carried out.

SUMMARY OF THE INVENTION

It is an object of the present invention to provide a rotary viscosimeter in which any damage to a pivot and its bearing can be prevented by contacting the pivot with the bearing on measurement and by separating the pivot from its bearing after completion of the measurement, these operations being automatically performed in response to an instruction without any complicated manipulation.

In order to provide the above-mentioned object, in an aspect of the present invention, there is provided in a rotary viscosimeter including a rotor which is driven to be rotated in a liquid, the viscosity of which is to be measured, a first drive shaft (rotor shaft) for supporting the rotor and for transmitting a rotary driving force to the rotor, rotary driving means having a driving power source for driving the rotor to be rotated and an output shaft for outputting the driving force, a second drive shaft for transmitting the driving force to the rotor shaft, a first link means for elastically linking the output shaft with the second drive shaft to transmit the driving force therebetween, support means having a pivot and a bearing for rotatably bearing support to the rotor shaft and second link means which by-passes the support means for linking the rotor shaft with the second shaft, the improvement comprising means for detecting the angular displacement between the output shaft and the rotor shaft; a pivot protection means having a locking mechanism for locking the rotor shaft against rotating and a pivot separating mechanism for separating and contacting between the pivot and the bearing of the support means, and control means for controlling the driving of the rotary driving means and the pivot protection means, the pivot protection means having a first state in which the rotor shaft is locked against rotating and the pivot of the supporting means is separated from the pivot and a second state that the pivot is in contact with the bearing and the locking of the rotor shaft is released, the control means having such a controlling capability that the pivot protection means is in the first and second states on termination and commencement of measurement, respectively.

The rotary viscosimeter of the present invention may include a first detection means for detecting that said pivot protection means is in the first state and second detection means for detecting that pivot protection means is in the second state.

The control means may have the capability of controlling the rotary driving means to be driven for rotating only when the pivot protection means is in the second state.

Specifically, the control means may have a capability of driving the locking mechanism in response to a measurement starting instruction in order to bring the pivot protection means to the second state until the second means detects that the pivot protecting means is in the second state and for driving the rotary driving means when the second detecting means detects that the pivot protection means is in the second state, and a capability of stopping the rotation of the rotary driving means in response to a measurement termination instruction and of driving the locking mechanism and the pivot separating mechanism to bring the pivot protection means to the first state until the first detecting means detects that the pivot protection means is in the first state.

In accordance with the present invention, the pivot is normally separated from the bearing when the viscosimeter is not in use. In order to use the viscosimeter, the pivot is brought into contact with its bearing. Then, the measurement of the viscosity is enabled. The pivot and its bearing can be thus protected.

From this, effects can be expected as follows:

(1) Deformation and damage of the pivot and its bearing caused by the removing and mounting operation of the prior or washing and cleaning of the rotor when the clamping operation has failed are prevented.

(2) Damage to the pivot and its bearing caused by vibrations and shocks generated on transportation or moving of the viscosimeter when the clamping operation has failed is prevented.

(3) It suffices to depress the starting and stopping push buttons in order to start and stop the viscosimeter. The operation of the viscosimeter is thus facilitated.

(4) Even an inexperienced person can easily operate the viscosimeter.

DETAILED DESCRIPTION OF THE PREFERRED EMBODIMENTS

The embodiment o the present invention will now be described with reference to drawings. It is to be understood that the present invention is not limited to only the following embodiments.

Figure 1:
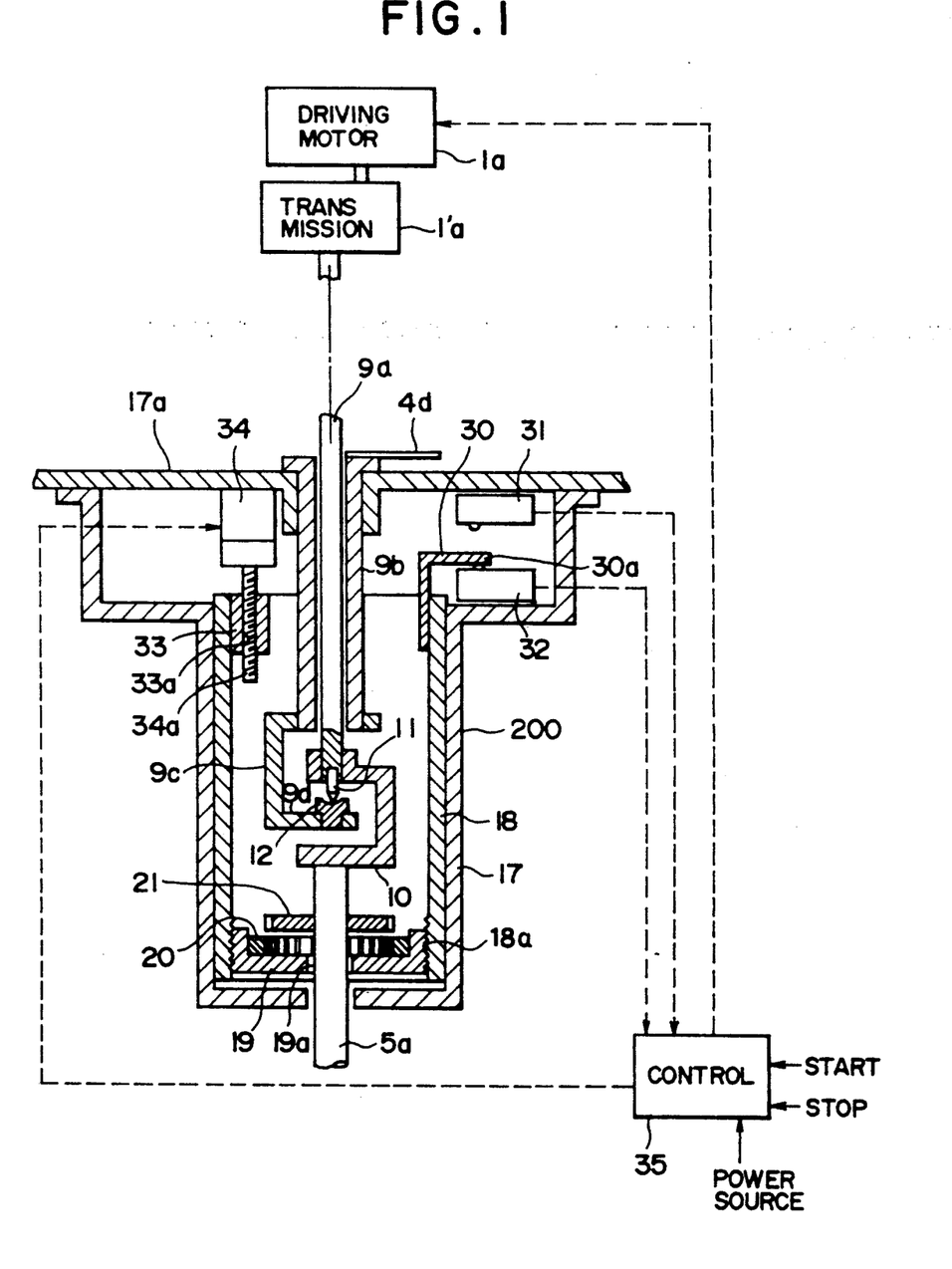
FIG. 1 is a sectional view showing the main part of a first embodiment of a rotary viscosimeter having a pivot protection apparatus of the present invention.
Figure 9:
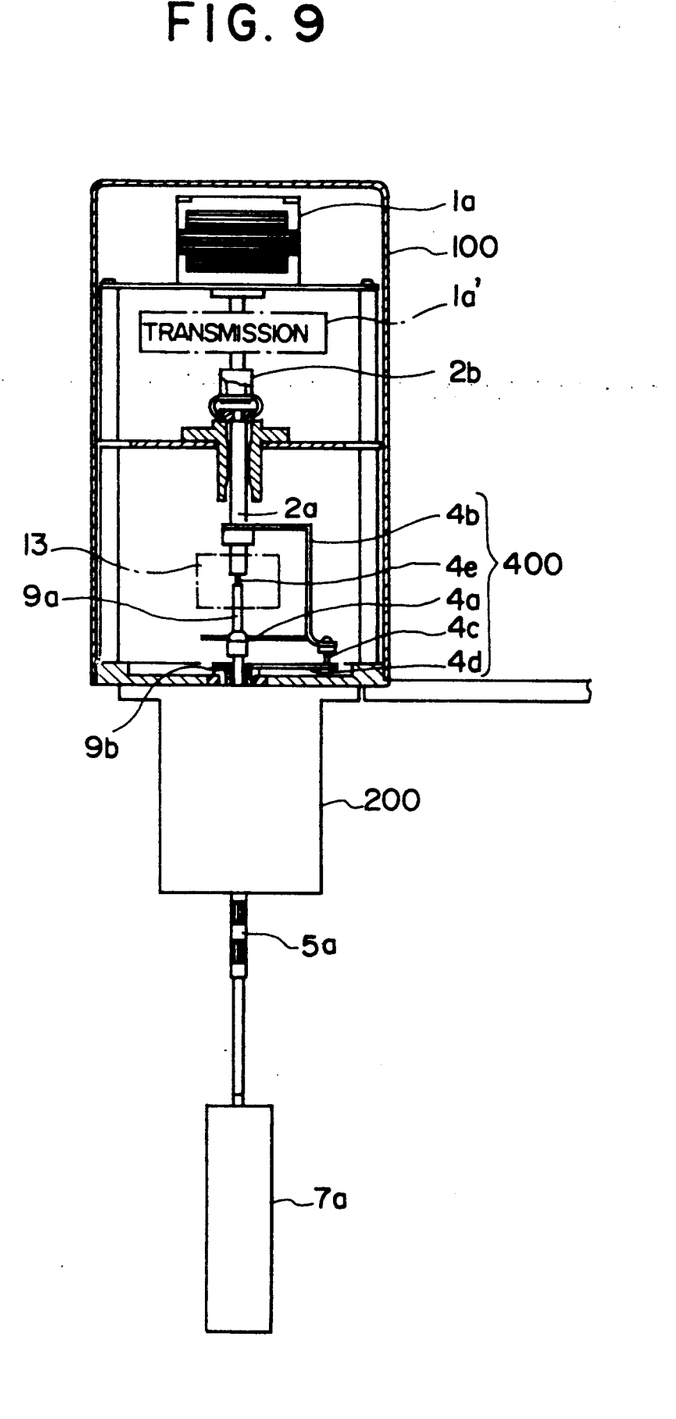
FIG. 9 is a schematic view showing the structure of the first embodiment of the rotary viscosimeter of the present invention.

An embodiment of a rotary viscosimeter of the present invention is schematically shown in FIG. 9 and a main part of the rotary viscosimeter is shown in FIG. 1.

As shown in FIG. 9, the rotary viscosimeter of the present invention comprises a rotor 7a, a rotor shaft 5a (a first driving shaft) for supporting and driving the rotor 7a in order to rotate the rotor, a main body 100 which drives the rotor 7a through the rotor shaft 5a and measures the viscosity and a pivot protection apparatus 200 which forms pivot protection means between the main body 100 and the rotor shaft 5a.

The main body 100 comprises a driving motor 1a, a transmission 1'a, a rotary coupling 2b and an output shaft 2a which form rotary driving means; a second driving shaft 9a having a lower end which is linked with the rotary shaft 5a in the pivot protection apparatus 200; a first link means 400 which elastically links the output shaft 2a with the second driving shaft 9a; and a rotary differential transformer 13 disposed between the output shaft 2a and a second driving shaft 9a, which serves as angular displacement detecting means.

The first link means 400 includes an L angle member 4b having one end which is connected in the vicinity of the lower end of the output shaft 2a, and a spiral spring 4a disposed between the other end of the L angle member 4b and a second driving shaft 9a. The first link means further includes an arm member 4d having one end linked with the L angle member 4b and the other end linked with a sleeve 9b which will be hereafter described for transmitting the rotary driving force of the output shaft 2a to the sleeve 9b. The first link means 400 further includes a pin 4e which is rotatably adapted in holes (not shown) formed on the end faces of the output shaft 2a and the second driving shaft 9a for preventing the second drive shaft 9 from oscillating.

The holes (not shown) formed on the end faces of the output shaft 2a and the second driving shaft 9a have such a depth that a slight axial displacement of the pin 4e corresponding to the axial displacements of the rotor shaft 5a and the second drive shaft 9a is absorbed.

The pivot protection apparatus 200 is shown in FIG. 1. The pivot protection apparatus 200 comprises a pivot 11 and a bearing 12 which form means for rotatably supporting and bearing the rotor shaft 9a, a channel type link means 10 serving as second link means which by-passes the pivot 11 and the bearing 12 for linking the rotary shaft 5a with a second driving shaft 9a, a locking mechanism and a pivot separating mechanism serving as pivot protecting means which will be described hereafter limit switches 31 and 32, respectively serving as first and second detecting means for detecting the condition of the pivot protecting means and an L-shaped fitting 30 which turns the limit switches 31 and 32 on or off. Most, but not all, of the foregoing parts are housed in a casing 17.

The pivot 11 is secured to the lower end of the second driving shaft 9a. On the other hand, the bearing 12 is secured to the lower side 9 of the channel type member 9c mounted on the lower end of the sleeve 9b surrounding the second driving shaft 9a. The pivot 11 and the bearing 12 are coaxially disposed. The sleeve 9b is rotatably supported on the upper flange 17a of the casing 17. As mentioned above, the arm member 4d is linked with the upper end of the sleeve 9b.

The sleeve 18 is housed in the casing 17 so that the sleeve 18 can be axially displaced. The sleeve 18 is formed with a thread 18a on the inner surface thereof in the lower part thereof. A disc plate 19 is threadably engaged with the thread 18a. The disc plate 19 is formed in the center thereof with a through-hole 19a through which a rotor shaft 5a freely passes. A first engaging member 20 (for example, an internal gear) is provided on the upper surface of the disc plate 19. A second engaging member 21 (for example, an external gear) which is engaged with the internal gear 20 is provided on the rotor shaft 5a.

The external gear 21 is mounted on the rotor shaft 5a in such a manner that when the internal gear 20 is displaced in association with the axial displacement of the sleeve 18, the external gear 21 is brought into engagement with the internal gear 20 and is brought into contact with the displacing disc 19 and is then displaced in an axial direction together with the rotor shaft 5a.

A block 33 which is provided with a screw hole 33a is mounted on the upper portion of the sleeve 18. On the other hand, a locking motor 34 is mounted on the flange portion 17a in such a position that the motor 34 faces the block 33. The motor 34 is provided with a threaded screw shaft 34a serving as an output shaft. The screw shaft 34a is threaded with the screw hole 33a of the block 33. The locking motor 34 rotates the screw shaft 34a in normal and reverse direction so that the block 33 is displaced upward and downward, respectively. The sleeve 18 is displaced in an axial direction by the displacement of the block 33.

The stroke of the displacement of the sleeve 18 is preset to such a length that separates the pivot 11 from the bearing 12. The other words, the stroke is preset to such a length that the internal gear 20 is displaced to engage with the outer gear 21 and the disc plate 19 is brought into contact with the outer gear 21 to lift the outer gear 21 upward for separating the pivot 11 from the bearing 12.

One side of the L angle fitting 30 is secured to the upper portion of the sleeve 18. The L angle fitting 30 is disposed so that the other side 30a projects externally from the sleeve 18 and is positioned between the above mentioned limit switches 31 and 32. That is, the side 30a is disposed in such a manner that it is displaced by the axial displacement of the sleeve 18 for turning the limit switches 31 and 32 on at the upper and lower extremities of its displacement, respectively. Accordingly, the limit switches 31 and 32 are separated by a spacing which is equal to the displacement stroke of the sleeve 18 plus the actuation strokes of both switches.

Figure 10:
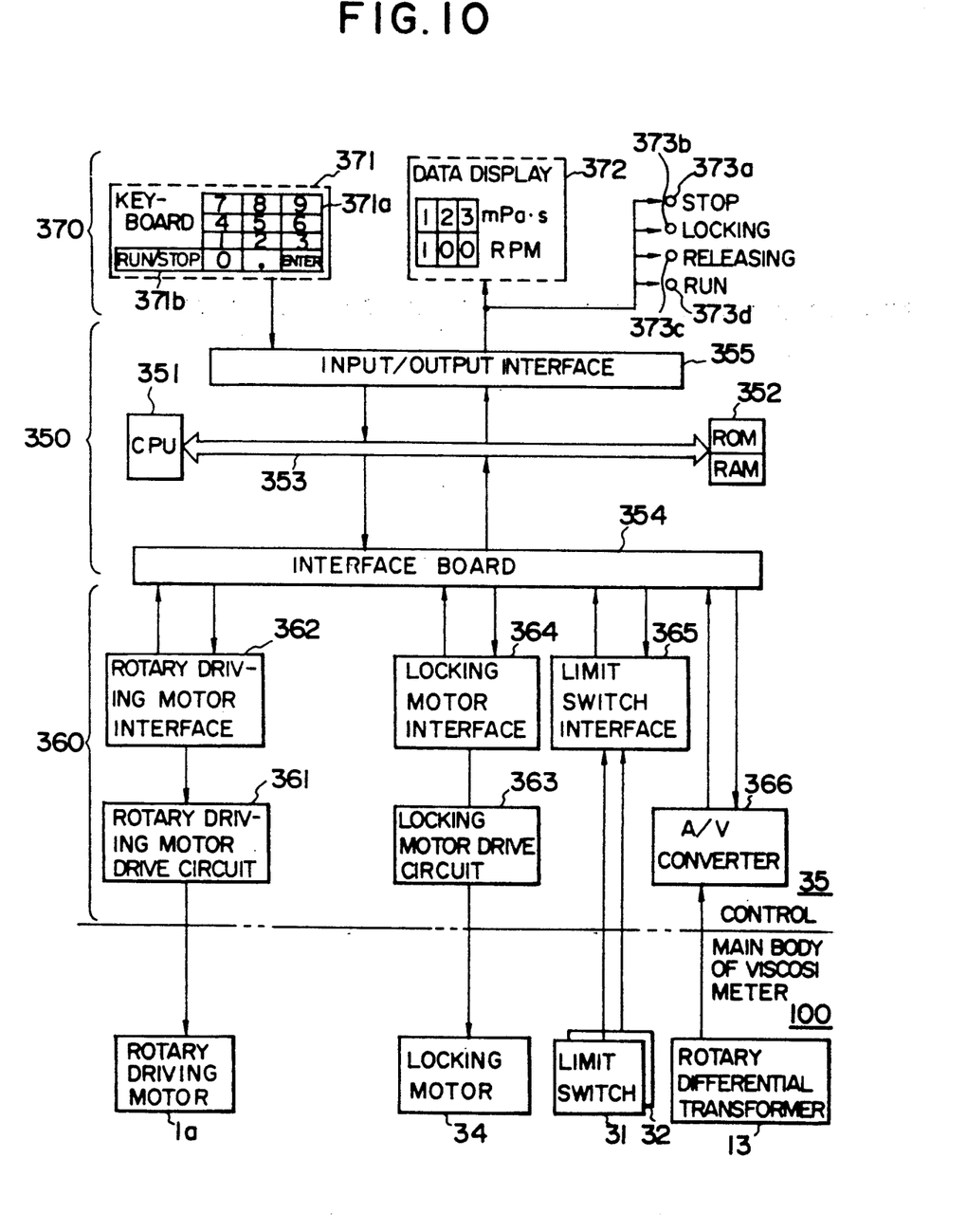
FIG. 10 is a block diagram showing an exemplary structure of the control used in the first embodiment of the present invention.

Referring now to FIG. 10, there is shown a control 35. The control 35 shown in FIG. 10 comprises a drive control 360 which is connected with the viscosimeter 100 for receiving measurement data and transmitting control data, an information processor unit 350 which performs processing of the measurement data from the driving control 360 and the control of operation of the driving control system and an input/output unit 370 for inputting and outputting information from and to the information processor unit 350.

The information processor unit 350 comprises a central processing unit (CPU) 351 for executing the control for measuring the viscosity and the processing of the measurement data, a memory 352 for storing therein programs executed by the CPU 351, various data and the results of processing, a data bus 353, an interface board (IB) 354 for controlling input and output of control signals, etc., and an input/output interface 355.

The memory 352 includes a ROM mainly for storing the programs and a RAM for storing data. The stored programs execute, for example, the steps as follows: receiving an externally inputted instruction for initiating measurement; driving the locking mechanism and the pivot separating mechanism in response to the instruction until the second detecting means detects that the pivot protection means is in the second condition; stopping the driving of the locking mechanism and the pivot separating mechanism and driving the rotary driving means when the second detecting means detects that the pivot protecting means is in the second condition; receiving an externally inputted instruction for terminating the measurement; stopping the driving of the rotary driving means in response to the instruction; and driving the locking mechanism and the pivot separating mechanism until the first detecting means detects that the pivot means is in the first condition.

Figure 11:
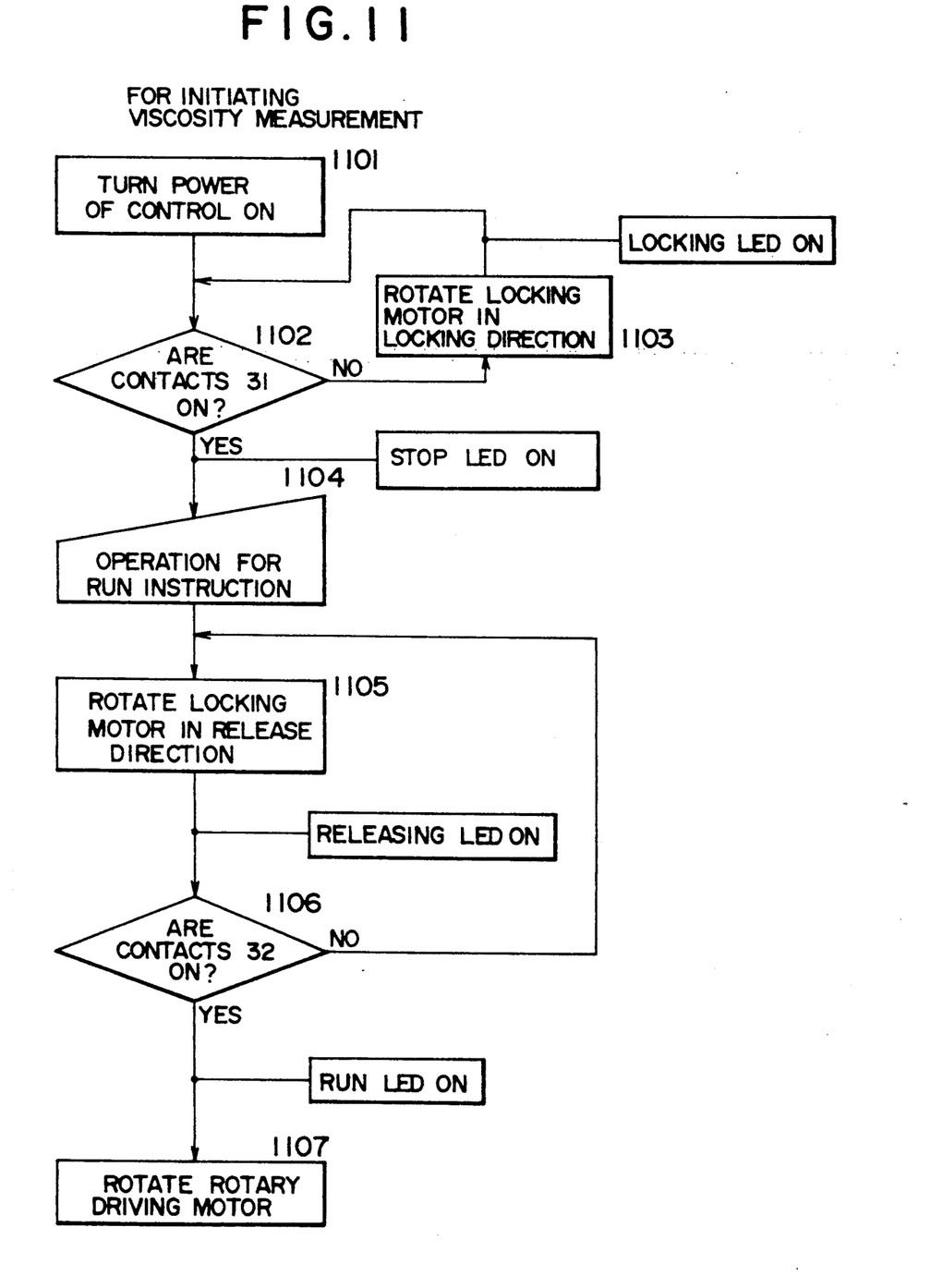
FIGS. 11 and 12 are flow charts showing the flow of operation of the control shown in FIG. 10.
Figure 12:
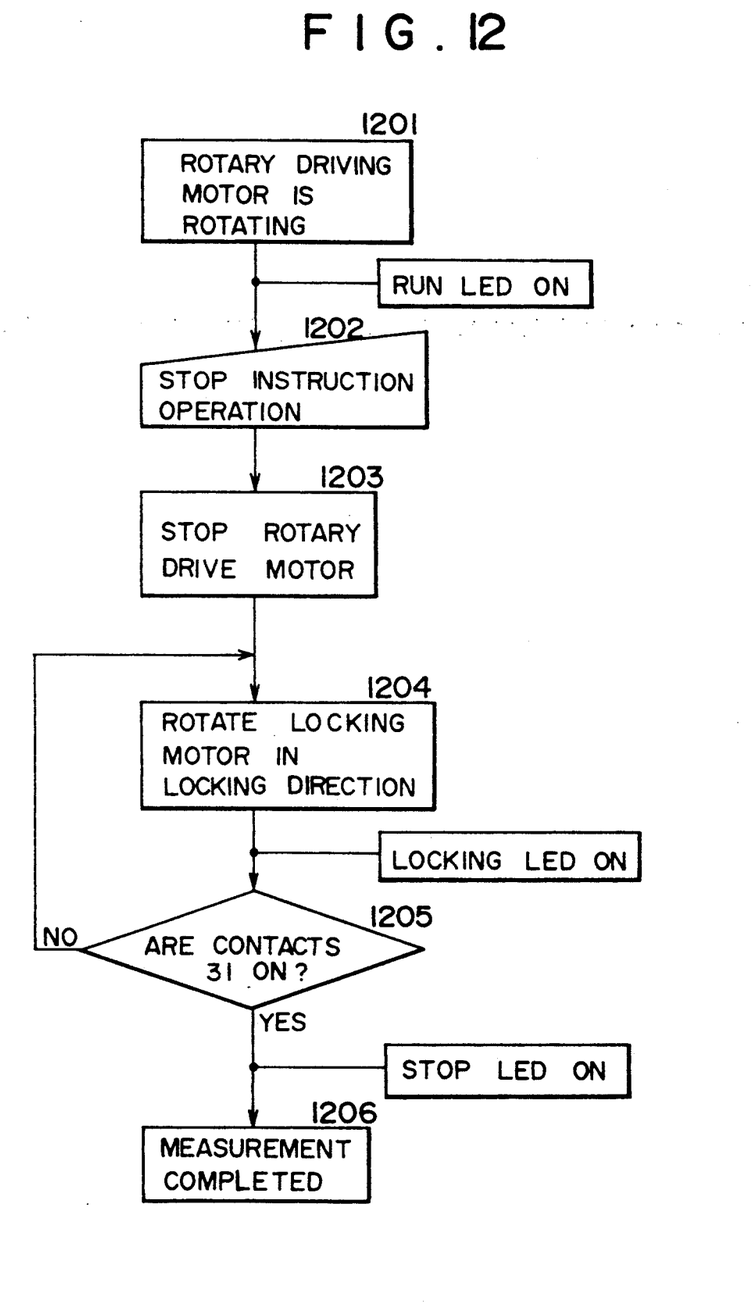

Detailed steps of this procedure are shown in FIGS. 11 and 12.

The driving control 360 comprises a rotary driving motor drive circuit 31, a rotary driving motor interface 362 for outputting a control signal from the information processor 350 to the drive circuit 361, a locking motor drive circuit 363 for driving a locking motor 34, a locking motor interface 364 for outputting a control signal from the information processor 350 to the locking motor drive circuit 363, a limit switch interface 365 of inputting turning on and off signals of the limit switches 31 and 32 to the information processor 350 and an A/D converter 366 for A/D converting the measurements of the rotary differential transformer 13 and for feeding the converted digital signals to the information processor 350.

The input/output unit 370 comprises a keyboard 371 for externally instructing execution/stop and for inputting and outputting data, etc. and a data display for displaying 372 information outputted from the information processor 350 and a status indicator 373.

The keyboard 371 includes ten keys 371a for inputting numerals and an execution/stop switch 371b for instructing execution/stop.

The measured viscosity and the rotational speed of the rotor are displayed by numerals on the data display 372. Numerical display elements such as LEDs are used for this display.

The status indicator 373 includes indicator elements 373a to 373d for indicating the status of the viscosimeter. LEDs may also be used for this indicator. Indicator elements (LED) 373a, 373b, 373c, and 373d light to indicate the states such as STOP, LOCKING, RELEASING and RUN, respectively.

The pivot protection apparatus 200 has at least two states, that is, a first state in which the rotor shaft 5a is locked and the pivot 11 is separated from the bearing 12 and a second state in which the rotor shaft 5a is unlocked. The control 35 controls the driving of the locking motor 34 in response to the external instruction so that the pivot protection apparatus 200 is brought into a desired state and controls the driving of the rotary driving motor 1a depending upon the state.

Figure 2:
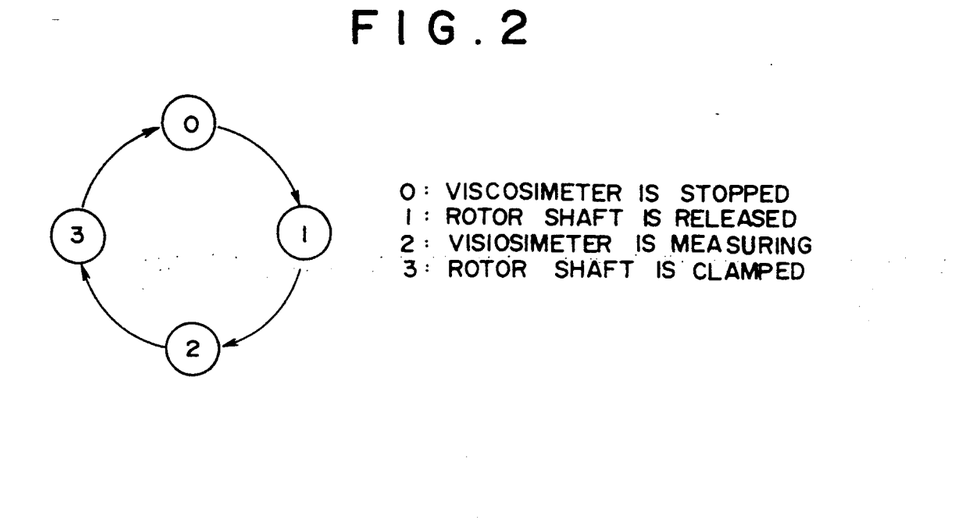
FIG. 2 is a state transition view showing each phases of the operation sequence of the embodiment of the viscosimeter.

Now, operation of the embodiment will be described with reference to FIGS. 2, 11 and 12. The rotary viscosimeter of the present embodiment changes its state in accordance with a series of sequences as shown in FIG. 2. State transition of each phase of a series of sequences is shown in FIG. 2. In FIG. 2, a numeral "0" represents a state where the viscosimeter is stopped. In this state, the pivot 11 is separated from the bearing 12 and the rotor shaft 5a is clamped against rotating. This state is the first. A numeral "2" represents a state in which the rotor shaft is rotating and the viscosimeter is measuring. In this state, the pivot 11 is in contact with the bearing 12 and the rotor shaft 5a is unlocked. This state is the second state. A numeral "3" in FIG. 2 represents a state in which the rotor shaft 5a is clamped.

Now, the series of operations will be described.

Firstly, operation of initiating the measurement of the viscosimeter will be described with reference to the flow chart of FIG. 11.

When the power to the control 35 is turned on for initiating the measurement (step 1101), the CPU 351 determines whether the contacts of the limit switch 31 are closed. This can be determined from a signal from the limit switch interface 365. If the limit switch 31 is turned off, an instruction is issued to the locking motor drive circuit 363 via the locking motor interface 364 for driving the locking motor 34 to lift up the sleeve 18 (step 1103). At this time, the CPU 351 lights the indicator element 373b. If the limit switch 31 is turned on, the locking motor 34 is not driven.

An input of an instruction for executing measurement is waited for in this state. If this instruction is inputted, the instruction is accepted (step 1104). The CPU 351 accepts this execution instruction and issues an instruction to drive the locking motor 34 in such a direction that the sleeve 18 is lowered (step 1105). At this time, the CPU 351 lights the indicator element 373c. The CPU continues this release operation until the limit switch 32 is turned on. The release operation is stopped and the indicator element 373d is lit when the limit switch 32 is turned on (step 1106). The CPU instructs the rotary driving motor drive circuit 361 via the rotary drive motor interface 362 to rotate the rotary drive motor 1a (step 1107).

Measurement of the viscosity is performed in this state. Measurement is achieved by detecting the angular displacement between the output shaft 2a and the second drive shaft 9a by the rotary differential transformer 13. The value measured by the rotary differential transformer 13 is converted into a digital value by the A/D converter 366 and is fed to the information processor 350 via the interface board 354.

The thus measured data is stored in, for example, the RAM of the memory 352 and is operated by the CPU 351. Both an operation result and the preliminarily set rotational speed of the rotor are displayed on the data display 372.

Now, operation for terminating the measurement of the viscosimeter will be described with reference to the flow chart in FIG. 12.

An input of a stop instruction from the execution/stop switch 371b is accepted (step 1202) while the rotary driving motor is rotating and the indicator element 373d is lift (step 1201).

When stop is instructed, the CPU 351 outputs an instruction to the rotary driving motor drive circuit 361 via the rotary driving motor interface 362 to stop the rotary driving motor 1a (step 1203).

The CPU 351 then outputs an instruction to the locking motor drive circuit 363 via the locking motor interface 364 for driving the locking motor 34 to lift up the sleeve 18 (step 1204). At this time, the CPU 351 lights the indicator element 373b and continues this locking operation until the limit switch 31 is turned on. When the limit switch 31 is turned on, the CPU stops the locking operation and lights the indicator element 373a (step 1205).

This terminates the measurement. In this state, the rotor shaft 5a is locked against rotating. The pivot 11 is separated from the bearing 12. Accordingly, damages to the pivot is prevented although washing and exchange operation of the rotor 7a is carried out. Since a series of steps until the pivot protection are automatically executed by only one instruction for termination of the measurement, washing of the unclamped rotor is prevented. Since the state of the viscosimeter is displayed, the user can easily recognize the operation condition of the viscosimeter so that incorrect operation is prevented.

Since the rotary driving motor is not driven while the locking motor is driven, carrying out a locking or releasing operation simultaneously with the viscosity measurement is prevented.

The embodiment in which the control comprises a computer has been described. The control is not limited to only the above mentioned structure. Another embodiment in which the structure of the control is different from that of the above mentioned embodiment will be described hereafter.

Figure 4:
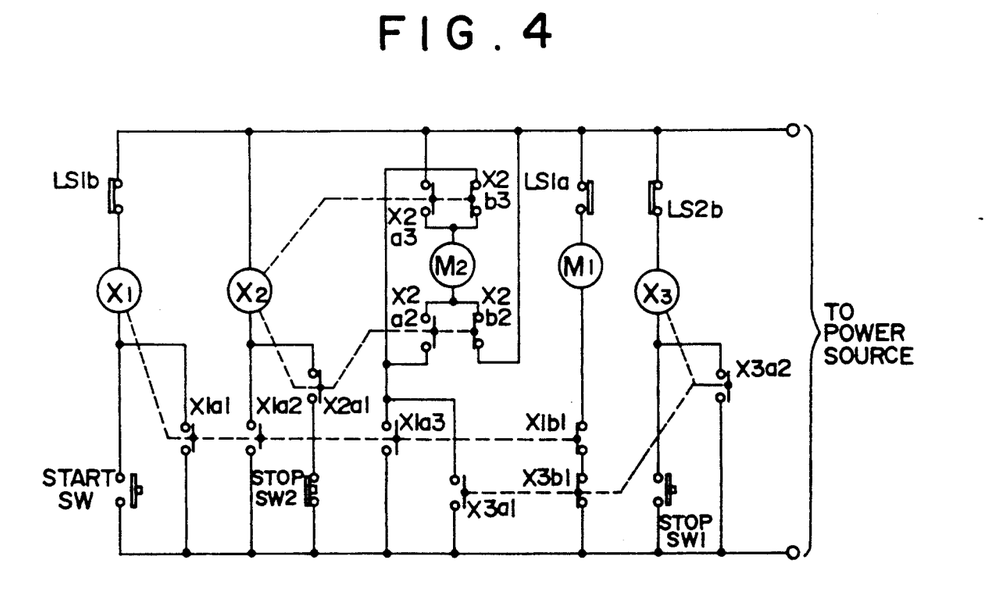
FIG. 4 is a circuit diagram of the control used in the second embodiment of the present invention.

A structure of the control in the second embodiment is shown in FIG. 4. The control shown in FIG. 4 comprises a sequence control circuit.

In FIG. 4, references START SW, STOP SW1, and STOP SW2 represents a starting push button switch, a stopping push button for a rotary driving motor and a locking switch for a locking motor, respectively. Reference M1 and M2 represent a rotary driving motor (rotary driving motor 1a in FIG. 1) and a locking motor (locking motor 34 in FIG. 1), respectively. X1, X2 and X3 represent relays. LS1a, LS1b, and LS2b represent contacts of limit switches. The stopping push button switches STOP SW1 and SW2 are formed so that they are complimentarily switched.

Figure 3:
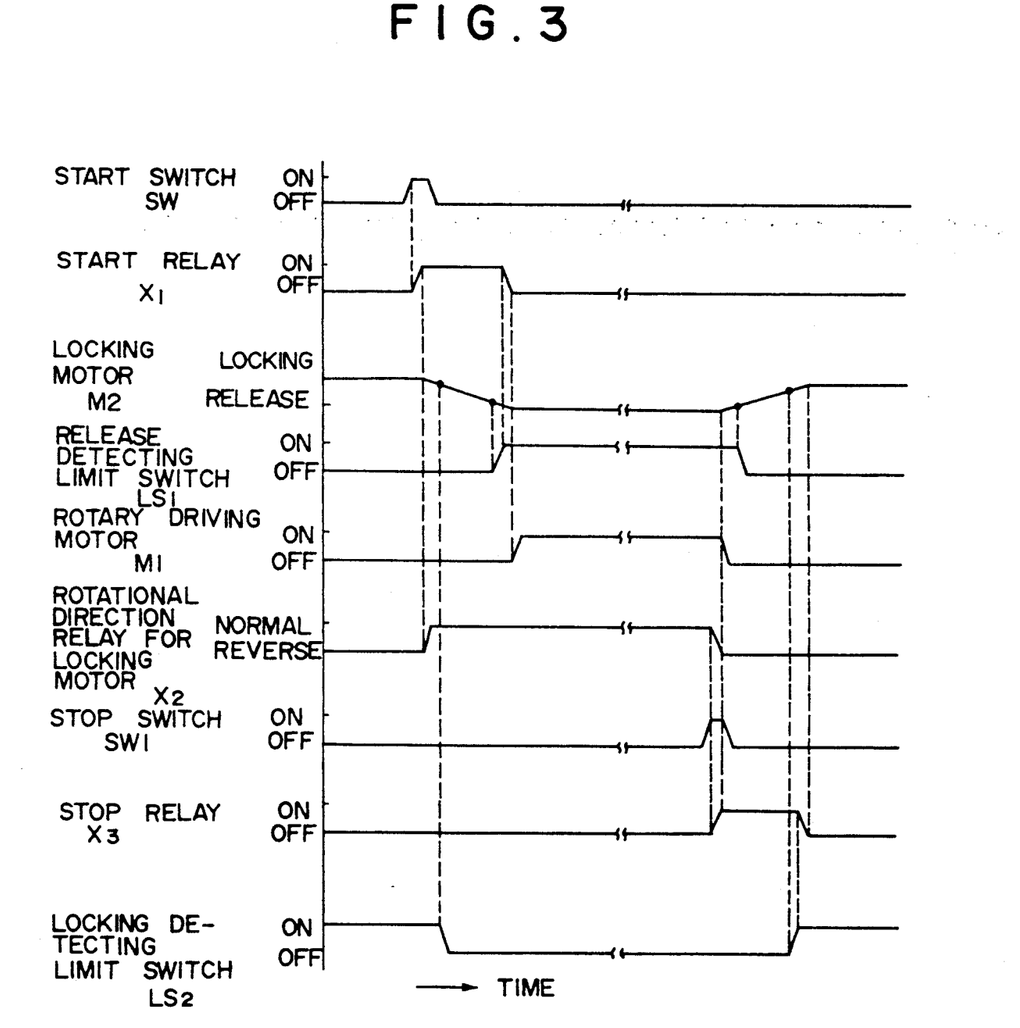
FIG. 3 is a time chart showing the sequence of operation performed by a control used in a second embodiment of the present invention.

Operation of the sequence control circuit will be described with reference to a flow chart in FIG. 3. The viscosimeter is identical with that shown in FIGS. 1 and 9. Accordingly operation of the control will be mainly described.

When the starting push button switch START SW is depressed, the start relay X1 is turned on so that the normally open contacts X1a1, X1a2, and X1a3 will be closed and the normally closed contacts X1b1 will be opened. This causes the rotary driving motor M1 to be turned off so that the motor M1 is brought into an interlock state whereby driving is prevented. The relay X2 is turned on so that the normally open contacts X2a1 are closed. The turning on of the relay X2 is thus self held. The normally open contracts X2a2 and X2a3 are closed and the normally closed contacts X2b1 and X2b2 are opened. This causes the locking motor M1 to be driven in a normal direction.

This operation lowers the sleeve 18 so that the rotor shaft 5a is released. When the limit switch LS1 (limit switch 32 in FIG. 1) detects the lower extremity of the sleeve 18, the normally open contacts LS1a are closed and the normally closed contacts LS1b are opened. The relay X1 is thus turned off an the normally open contacts X1a1, X1a2, and X1a3 are opened and the normally closed contacts X1b1 are closed. This causes the locking motor M2 to be stopped and the rotary driving motor M1 to be rotated.

When the stopping push button switch STOP SW1 is depressed to be turned on in order to terminate the measurement, the stopping push button switch STOP SW 2 is turned off so that the self-holding of the relay X2 is released to change the rotational direction of the motor M2. Simultaneously with this, the relay X3 is turned on to be self held and to open the normally closed contacts X3b1 for stopping the rotary driving motor M1. The normally open contacts X3a1 are closed to drive the locking motor M2.

The sleeve 18 is lifted up by the locking motor 12 for locking the rotor shaft 5a and separating the pivot 11 from the bearing 12. When the limit switch LS2 detects the upper extremity of lifting of the sleeve 18, the normally closed contacts LS2b are opened for turning the relay X3 off. This causes the locking motor M2 to be stopped so that a series of operations are completed. Also in the above second embodiment, protection of the pivot is automatically performed after completion of the measurement similarly to the first embodiment. It suffices to instruct starting for commencing the measurement. Accordingly, operation is easy.

In the foregoing embodiment, the locking motors are used as actuators and axial displacement of the sleeve is achieved by the motor. In the present invention the actuator is not limited to such a motor. Any means which is capable of providing a necessary displacement stroke, such as a linear motor and solenoid may be used.

Although the limit switch used in the foregoing embodiments is a micro-switch, the limit switch is not limited to only such a micro-switch. For example, position detecting sensors such as optical switches, magnetic switches and pressure sensitive switches, etc. may be used. If the displacement of the sleeve is constant, the limit switches may be omitted.

Though the invention has been described with respect to a specific preferred embodiment thereof, many variations and modifications will immediately become apparent to those skilled in the art. It is therefore the intention that the appended claims be interpreted as broadly as possible in view of the prior art to include all such variations and modifications.

What is claimed is:

1. In a rotary viscosimeter including a rotor which is driven to be rotated in a liquid, the viscosity of which is to be measured, a first drive shaft (rotor shaft) for supporting the rotor and for transmitting a rotary driving force to the rotor, rotary driving means having a driving power source for driving the rotor to be rotated and an output shaft for outputting the driving force, a second drive shaft for transmitting the driving force to the rotor shaft, a first link means for elastically linking the output shaft with the second drive shaft to transmit the driving force therebetween, support means having a pivot and a bearing for rotatably bearing to support the rotor shaft and second link means which by-passes the support means for linking the rotor shaft with the second shaft, the improvement comprising:

means for detecting the angular displacement between the output shaft and the rotor shaft;

a pivot protection means having a locking mechanism for locking the rotor shaft against rotating and releasing the locking of the rotor shaft and a pivot separating mechanism for separating and contacting between the pivot and the bearing of the support means; and control means for controlling the driving of the rotary driving means and the pivot protection means, the pivot protection means having a first state in which the rotor shaft is locked against rotating and the pivot of the supporting means is separated from the pivot and a second state in which the pivot is in contact with the bearing and the locking of the rotor shaft is released, the control means having such a capability of controlling that the pivot protection means is in the first and second states on termination and commencement of measurement, respectively.

2. A rotary viscosimeter as defined in claim 1 and further including a first detection means for detecting that said pivot protection means in the first state and second detection means for detecting that said pivot protection means in the second state.

3. A rotary viscosimeter as defined in claim 2 in which said control means has a capability of controlling the rotary driving means to be driven for rotating only when said pivot protection means is in the second state.

4. A rotary viscosimeter as defined in claim 2 in which said control means has a capability of driving said locking mechanism in response to a measurement starting instruction to bring the pivot protection means to the second state until the second means detects that the pivot protecting means in the second state and for driving the rotary driving means when the second detecting means detects that the pivot protection means in the second state, and a capability of stopping the rotation of the rotary driving means in response to a measurement termination instruction and of driving the locking mechanism and the pivot separating mechanism to bring the pivot protection means to the first state until the first detecting means detects that the pivot protection means is in the first state.

5. A rotary viscosimeter as defined in claim 4 and further including display means for displaying operation conditions.

6. A rotary viscosimeter as defined in claim 5 in which the display means receives a signal representative of states from said control means.

7. A rotary viscosimeter as defined in claim 1 in which said control means includes at least a memory for storing therein a control program for controlling the operation of said rotary driving means and pivot protection means and a central processing unit for executing the control program stored in the memory.

8. A rotary viscosimeter as defined in claim 1 in which said first link means includes a spiral spring for elastically linking said rotary driving means with the second driving shaft.

9. A rotary viscosimeter as defined in claim 1 in which said angular displacement means includes a rotary differential transformer for electrically detecting the angular displacement.

10. A method of operating a rotary viscosimeter, the rotary viscosimeter including a rotor which is driven to be rotated in a liquid, the viscosity of which is to be measured, a first drive shaft for supporting the rotor and for transmitting a rotary driving force to the rotor, rotary driving means having a driving power source for driving the rotor to be rotated and an output shaft for outputting the driving force, a second drive shaft for transmitting the driving force to the rotor shaft, a first link means for elastically linking the output shaft with the second drive shaft to transmit the driving force therebetween, support means having a pivot and a bearing for rotatably bearing to support the rotor shaft and second link means which by-passes the support means for linking the rotor shaft with the second shaft, means for detecting the angular displacement between the output shaft and the rotor shaft;

a pivot protection means having a locking mechanism for locking the rotor shaft against rotating and releasing the locking of the rotor shaft and a pivot separating mechanism for separating and contacting between the pivot and the bearing of the support means; and control means for controlling the driving of the rotary driving means and the pivot protection means, the pivot protection means having a first state in which the rotor shaft is locked against rotating and the pivot of the supporting means is separated from the pivot and a second state in which the pivot is in contact with the bearing and the locking of the rotor shaft is released, the control means having such a capability of controlling that the pivot protection means is in the first and second states on termination and commencement of measurement, respectively, wherein the control means includes at least a memory for storing therein a control program for controlling the operation of said rotary driving means and pivot protection means and the central processing unit for executing the control programs stored in the memory, the method including the steps of:

receiving an externally inputted instruction for initiating measurement; driving the locking mechanism and the pivot separating mechanism in response to the instruction until the pivot protection means is in the second state;

stopping the driving of the locking mechanism and the pivot separating mechanism and driving the rotary driving means when the second detecting means detects that the pivot protecting means in the second state;

receiving an externally inputted instruction for terminating the measurement;

stopping the driving of the rotary driving means in response to the instruction; and driving the locking mechanism and the pivot separating mechanism until the pivot protection means is in the first state.

* * * * *